US007847547B2

(12) United States Patent
Markley et al.

(10) Patent No.: US 7,847,547 B2
(45) Date of Patent: Dec. 7, 2010

(54) METHOD AND SYSTEM FOR DETERMINING COMPOUND CONCENTRATIONS IN A MIXTURE USING REGRESSION OF NMR INTENSITY PEAK VALUES

(75) Inventors: John L. Markley, Madison, WI (US);
Ian A. Lewis, Madison, WI (US);
William M. Westler, Madison, WI (US);
Qiu Cui, Madison, WI (US); Gabriel Cornilescu, Madison, WI (US); Marco Tonelli, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 331 days.

(21) Appl. No.: 12/022,465

(22) Filed: Jan. 30, 2008

(65) Prior Publication Data

US 2009/0192725 A1    Jul. 30, 2009

(51) Int. Cl.
*G01V 3/00* (2006.01)
(52) U.S. Cl. .................. 324/307; 324/303; 324/306; 324/309; 324/318; 324/321
(58) Field of Classification Search ......... 324/300–322; 702/23; 600/407–435
See application file for complete search history.

(56) References Cited

U.S. PATENT DOCUMENTS

| | | | | | |
|---|---|---|---|---|---|
| 3,238,446 | A | * | 3/1966 | Zimmerman | ................ 324/303 |
| 4,081,742 | A | * | 3/1978 | Hofer et al. | ................ 324/307 |
| 5,510,895 | A | * | 4/1996 | Sahagen | ................ 356/436 |
| 6,696,838 | B2 | * | 2/2004 | Raftery et al. | ................ 324/321 |
| 6,898,453 | B2 | * | 5/2005 | Lee | ................ 600/407 |
| 6,937,014 | B2 | * | 8/2005 | Sun et al. | ................ 324/303 |
| 7,529,576 | B2 | * | 5/2009 | Keller et al. | ................ 600/431 |
| 7,557,573 | B2 | * | 7/2009 | Ardenkjaer-Larsen et al. | ................ 324/309 |
| 7,709,266 | B2 | * | 5/2010 | Mayer et al. | ................ 436/173 |
| 2002/0130661 | A1 | * | 9/2002 | Raftery et al. | ................ 324/318 |
| 2004/0189296 | A1 | * | 9/2004 | Sun et al. | ................ 324/306 |
| 2004/0249275 | A1 | * | 12/2004 | Keller et al. | ................ 600/431 |
| 2008/0058636 | A1 | * | 3/2008 | Caravan et al. | ................ 600/414 |
| 2009/0192725 | A1 | * | 7/2009 | Markley et al. | ................ 702/23 |

OTHER PUBLICATIONS

Lewis, Ian, et al., "Method for Determining Molar Concentrations of Metabolites in Complex Solutions from Two-Dimensional $^1H$-$^{13}C$ NMR Spectra," American Chemical Society, Analytical Chemistry, vol. 79, No. 24, Dec. 15, 2007, pp. 9385-9390.

* cited by examiner

*Primary Examiner*—Melissa J Koval
*Assistant Examiner*—Tiffany A Fetzner
(74) *Attorney, Agent, or Firm*—Bell & Manning, LLC (57) ABSTRACT

A method of determining a concentration level of a compound in a mixture is provided. A plurality of compounds are identified in the mixture based on intensity peaks identified from NMR data generated from the mixture. A compound is selected from the identified plurality of compounds for a concentration determination. A concentration equation associated with the selected compound is determined. A first peak associated with the selected compound is selected from the NMR data. The selected first peak does not overlap with a peak associated with another compound of the identified plurality of compounds. An intensity value associated with the selected first peak is determined. A concentration of the selected compound in the mixture is calculated using the determined concentration equation and the determined intensity value.

26 Claims, 8 Drawing Sheets

METHOD AND SYSTEM FOR DETERMINING COMPOUND CONCENTRATIONS IN A MIXTURE USING REGRESSION OF NMR INTENSITY PEAK VALUES

REFERENCE TO GOVERNMENT RIGHTS

This invention was made with United States government support awarded by the following agencies: National Institutes of Health Award Nos. DK070297, RR002301, GM066323. The United States government has certain rights in this invention.

FIELD

The field of the disclosure relates generally to nuclear magnetic resonance spectroscopy. More specifically, the disclosure relates to a method and a system for determining compound concentrations in a mixture using nuclear magnetic resonance spectroscopy.

BACKGROUND

Nuclear magnetic resonance (NMR) spectroscopy utilizes the magnetic properties of nuclei to provide information on the chemical characteristics of a molecule. When placed in a magnetic field, NMR active nuclei absorb and emit energy at a frequency characteristic of the isotope. Typically, a target is placed in a strong magnetic field that causes the generally disordered and randomly oriented nuclear spins of the atoms to become aligned with the applied magnetic field. One or more radio frequency (RF) pulses are transmitted into the target, perturbing the nuclear spins. As the nuclear spins relax to their aligned state, the nuclei emit RF energy that is detected by receiving coils arranged about the target. The energy absorption and the intensity of the resulting signal are proportional to the strength of the magnetic field.

Depending on the local chemical environment, different protons in a molecule resonate at slightly different frequencies. Because the frequency is proportional to the strength of the magnetic field, it can be converted into a field-independent dimensionless value known as a chemical shift. The chemical shift may be reported as a relative measure from a reference resonance frequency. For example, the chemical shift may be determined as a difference between the frequency of the signal and the frequency of the reference divided by the frequency of the reference signal. Commonly measured reference nuclei are hydrogen-1 ($^1H$) and carbon-13 ($^{13}C$), though nuclei from isotopes of many other elements can also be used as references. The frequency shifts generally are extremely small (typically hundreds of Hertz) in comparison to the frequency of the reference signal (typically hundreds of megahertz), and thus, are generally expressed as parts per million (ppm).

Figure 1:
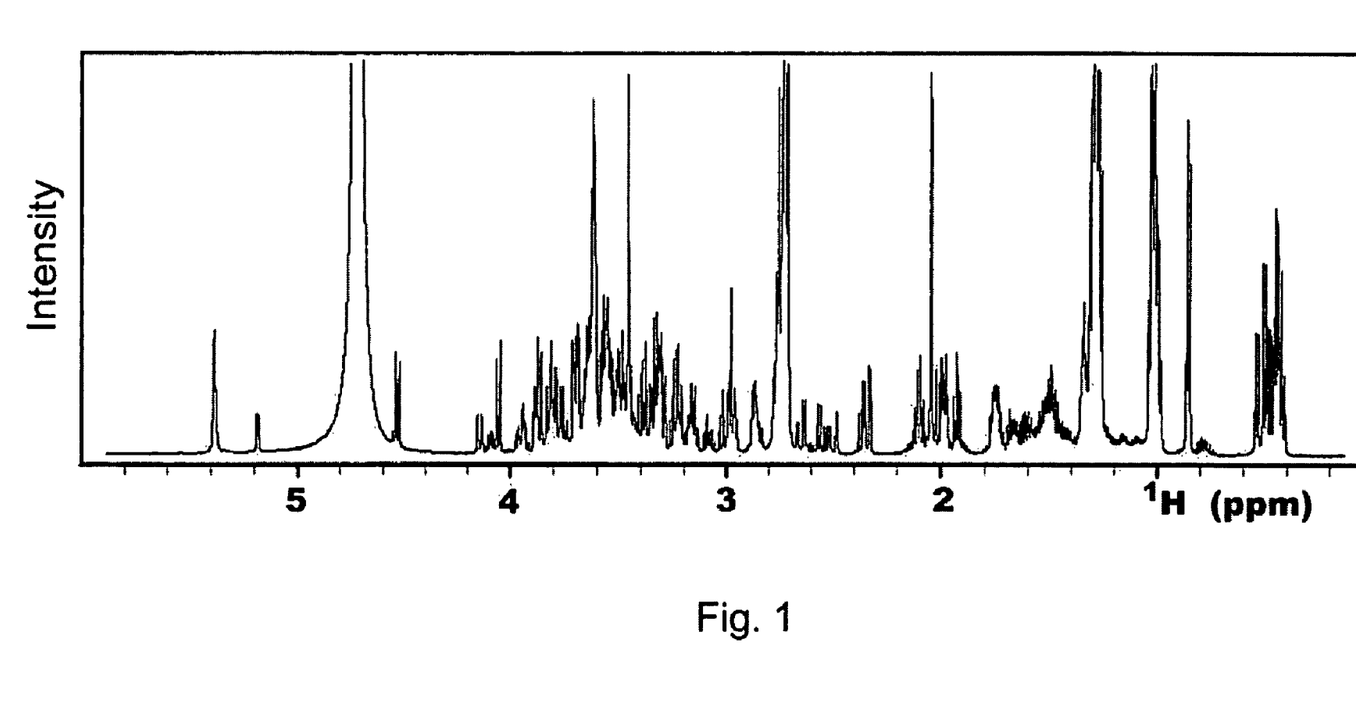
FIG. 1 depicts an example 1D $^1$H NMR spectrum of an equimolar mixture of 26 small molecule standards.
Figure 2:
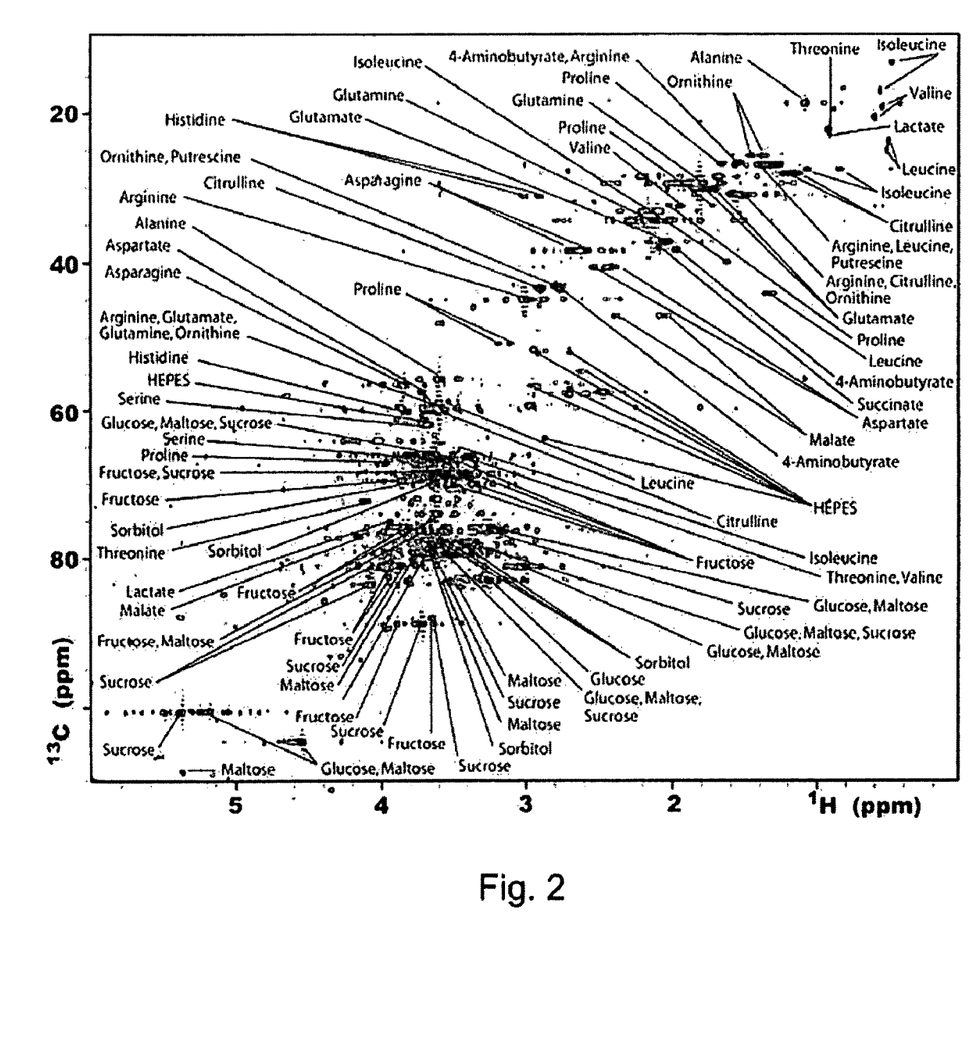
FIG. 2 depicts an example 2D $^1$H-$^{13}$C NMR spectrum of the equimolar mixture shown in FIG. 1 overlaid onto a spectrum of aqueous whole-plant extract from *Arabidopsis thaliana*.

Analysis of a one-dimensional (1D) NMR spectrum provides information related to the number and the type of chemical entities in a molecule. For example, with reference to FIG. 1, a 1D NMR spectrum is shown of an equimolar mixture of twenty-six small molecule standards using a $^1H$ reference nuclei. Multi-dimensional NMR involves a series of 1D experiments. Each experiment consists of a sequence of RF pulses with delay periods between each sequence. The use of pulses of different shapes, frequencies, intensities, and durations in specifically-designed patterns or pulse sequences allows a determination of different types of information about the molecule and distinguishes different multi-dimensional NMR types. For example, there are multiple types of two-dimensional (2D) NMR spectroscopy including correlation spectroscopy, J-spectroscopy, exchange spectroscopy, nuclear Overhauser effect spectroscopy, total correlation spectroscopy, heteronuclear correlation experiments, etc. Heteronuclear correlation experiments may include heteronuclear single quantum coherence (HSQC), heteronuclear multiple quantum coherence (HMQC), heteronuclear multiple bond correlation (HMBC), etc. 2D NMR spectrum provide more information about a molecule than 1D NMR spectra. For example, with reference to FIG. 2, a 2D NMR spectra is shown of the equimolar mixture of twenty-six small molecule standards shown in FIG. 1 overlaid onto a spectrum of aqueous whole-plant extract from *Arabidopsis thaliana*. Peaks from covalently bonded 1H-13C pairs are identified on the basis of simultaneously satisfying positions on the x-axis (frequency of the $^1H$ nucleus) and y-axis (frequency of the $^{13}C$ nucleus).

1D $^1H$ NMR spectroscopy has been used as an analytical tool for identifying small molecules and measuring their concentrations. Traditionally, quantitative analysis by NMR has been restricted to relatively simple mixtures with minimal peak overlap because overlapped peaks do not scale in a discrete linear fashion that typifies well-isolated peaks. Instead, overlapped peaks scale as the sum of the total overlapped resonance. As a result, multivariate and correlation statistics are reporters of overlapped spectral density rather than the concentrations of specific compounds. Thus, although peak overlap does not interfere with the reproducibility of traditional analyses, it does prevent accurate quantification.

Recently, interest has surged in using NMR for high-throughput analysis of complex biological processes at the metabolic level. These studies, defined as "metabolomics" or "metabonomics", place an emphasis on biomarker discovery or disease classification and are typically centered on unfractionated biological fluids and tissue extracts. 1D $^1H$ NMR spectra of these types of samples typically contain hundreds of overlapping resonances (see FIG. 1) that make traditional NMR-based analytical practices, such as resonance assignment and accurate peak integration, impossible or impractical.

Using 2D $^1H$-$^{13}C$ NMR (see FIG. 2), peak overlap is reduced. However, applications of multidimensional NMR in the metabolomics literature have been largely restricted to qualitative analyses generally for two reasons. The first reason is that 2D $^1H$-$^{13}C$ cross-peak intensities (or volumes) are influenced by a greater number of variables (e.g. uneven excitation, non-uniform relaxation, evolution times, mixing times, etc.) than are 1D $^1H$ NMR peaks. The non-uniform behavior makes it difficult to translate peak intensities into metabolite concentrations. A second reason is that 2D $^1H$-$^{13}C$ NMR spectra usually require more time to collect than 1D $^1H$ spectra. Long acquisition times are impractical for metabolomics studies that require the analysis of hundreds of samples. Thus, a method and a system to support metabolomics studies using NMR data is needed.

SUMMARY

In an exemplary embodiment, a method of determining a concentration of a compound in a mixture is provided. A plurality of compounds are identified in the mixture based on intensity peaks identified from NMR data generated from the mixture. The NMR data is two-dimensional heteronuclear single quantum coherence NMR data. A compound is selected from the identified plurality of compounds for a concentration determination. A concentration equation associated with the selected compound is determined. A first peak associated with the selected compound is selected from the NMR data. The selected first peak does not overlap with a peak associated with another compound of the identified plurality of compounds. An intensity value associated with the selected first peak is determined. A concentration of the selected compound in the mixture is calculated using the determined concentration equation and the determined intensity value.

In another exemplary embodiment, a computer-readable medium is provided comprising computer-readable instructions that, upon execution by a processor, cause the processor to perform the operations of the method of determining a concentration of a compound in a mixture.

In another exemplary embodiment, a device is provided. The device includes, but is not limited to, a processor and the computer-readable medium. The computer-readable medium operably couples to the processor. The computer-readable medium comprises instructions that, upon execution by the processor, perform the operations of the method of determining a concentration of a compound in a mixture.

In another exemplary embodiment, a method of defining a concentration equation for a compound is provided. First NMR data of a first mixture of pure compounds selected from a plurality of compounds is collected. A first concentration for each of the pure compounds in the first mixture is known. For each of the pure compounds, a first non-overlapping peak is selected from the collected first NMR data. A first intensity value associated with each selected first non-overlapping peak is determined. Second NMR data for a second mixture of the pure compounds is collected. A second concentration for each of the pure compounds in the second mixture is known. Additionally, the second concentration is different from the first concentration. For each of the pure compounds, a second non-overlapping peak from the collected second NMR data is selected. A second intensity value associated with each selected second non-overlapping peak is determined. A concentration equation for each compound of the pure compounds is determined using the determined first intensity value associated with each compound at the first concentration and the determined second intensity value associated with each compound at the second concentration.

In another exemplary embodiment, a computer-readable medium is provided comprising computer-readable instructions that, upon execution by a processor, cause the processor to perform the operations of the method of defining a concentration equation for a compound.

In another exemplary embodiment, a device is provided. The device includes, but is not limited to, a processor and the computer-readable medium. The computer-readable medium operably couples to the processor. The computer-readable medium comprises instructions that, upon execution by the processor, perform the operations of the method of defining a concentration equation for a compound.

Other principal features and advantages of the invention will become apparent to those skilled in the art upon review of the following drawings, the detailed description, and the appended claims.

BRIEF DESCRIPTION OF THE DRAWINGS

Exemplary embodiments of the invention will hereafter be described with reference to the accompanying drawings, wherein like numerals denote like elements.

DETAILED DESCRIPTION

Figure 3:
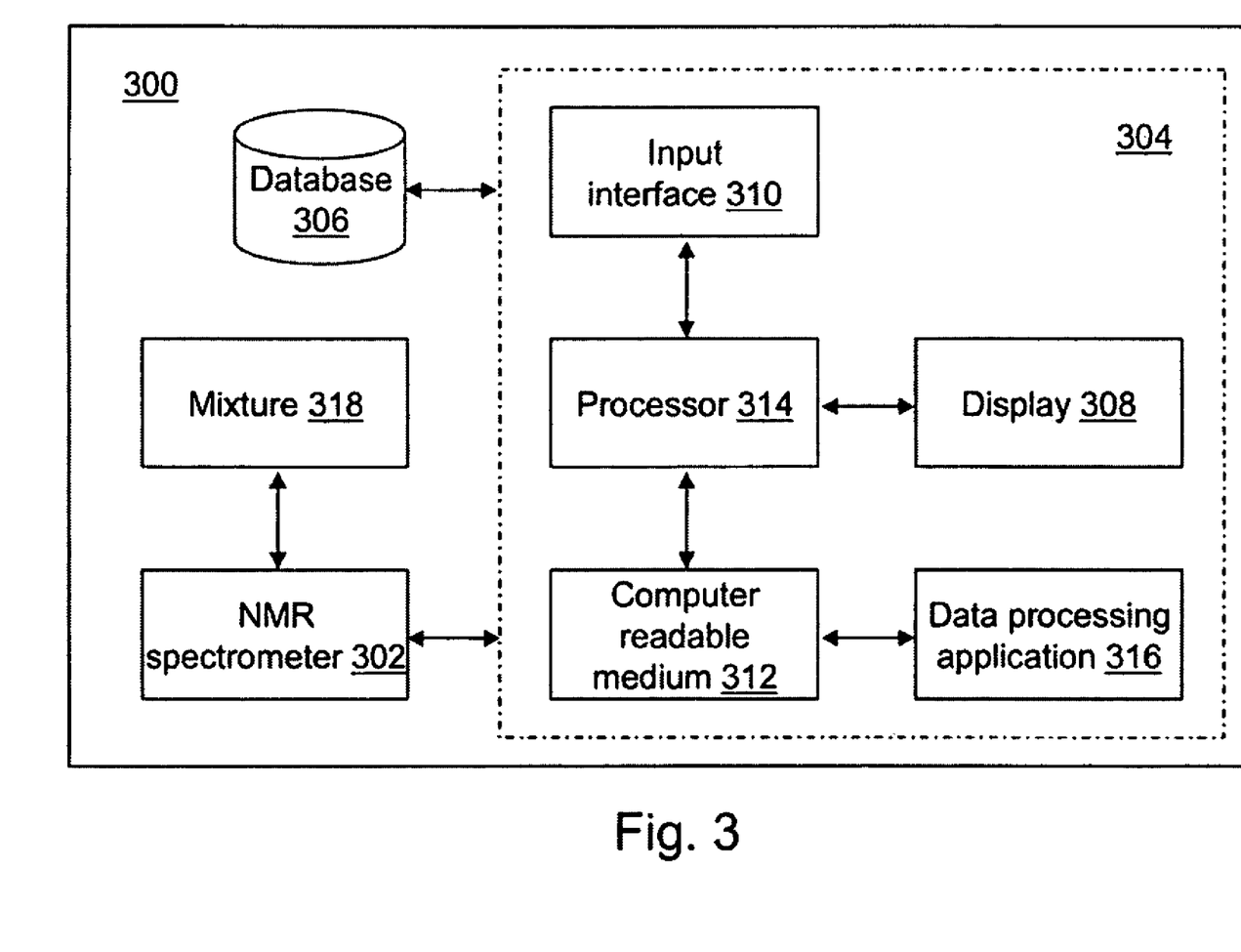
FIG. 3 depicts a block diagram of an NMR data processing system in accordance with an exemplary embodiment.

With reference to FIG. 3, a block diagram of an NMR data processing system 300 is shown in accordance with an exemplary embodiment. NMR data processing system 300 may include a nuclear magnetic resonance (NMR) spectrometer 302, a computing device 304, and a database 306. In an exemplary embodiment, NMR spectrometer 302 is a 600 megahertz (MHz) spectrometer with a triple-resonance ($^1$H, $^{13}$C, $^{15}$N, $^2$H, lock) cryogenic probe and a sample changer that processes a mixture 318. Exemplary spectrometer manufacturers include Varian, Bruker, Siemens, JEOL, Philips, etc. NMR spectrometers of a different type, field strength, manufacture, and model may be used in alternative embodiments without limitation. Mixture 318 may include a variety of chemical compounds.

NMR spectrometer 302, computing device 304, and database 306 may be integrated into a single device. Alternatively, NMR spectrometer 302, computing device 304, and/or database 306 may be implemented in a plurality of devices. For example, computing device 304 and database 306 may be implemented in a single device. NMR spectrometer 302, computing device 304, and/or database 306 may be connected directly. For example, NMR spectrometer 302 may connect to computing device 304 using a cable for transmitting information between NMR spectrometer 302 and computing device 304. In another exemplary embodiment, NMR spectrometer 302 may connect to computing device 304 using a network that may be wired and/or wireless. In another exemplary embodiment, NMR spectrometer 302 and computing device 304 may not be connected. Instead, NMR data acquired using NMR spectrometer 302 may be manually provided to computing device 304. For example, the NMR data may be stored on electronic media such as, but not limited to, a compact disc (CD) or a digital video disc (DVD). After receiving the NMR data, computing device 304 may initiate processing of the NMR data based on a user input at computing device 304 or automatically without user input.

Computing device 304 includes or can access database 306 either through a direct connection or through a network that is wired and/or wireless. Database 306 may include a plurality of databases that may be organized into multiple database tiers to improve data management and access. Database 306 is a data repository for NMR data processing system 300. Database 306 may utilize one or more database technologies as known to those skilled in the art including a file system, a relational database, a system of tables, etc.

Computing device 304 may include a display 308, an input interface 310, a computer-readable medium 312, a processor 314, and a data processing application 316. Computing device 304 may be a computer of any form factor. Different and additional components may be incorporated into computing device 304. Components of NMR data processing system 300 may be included in a single device or included in multiple devices positioned in a single location, a single facility, and thus, may be remote from one another. As a result, computing device 304 may include a communication interface, which provides an interface for receiving and transmitting data between devices using various protocols, transmission technologies, and media as known to those skilled in the art. The communication interface may support communication using various transmission media that may be wired and/or wireless.

Display 308 presents information to a user of computing device 304 as known to those skilled in the art. For example, display 308 may be a thin film transistor display, a light emitting diode display, a liquid crystal display, or any of a variety of different displays known to those skilled in the art now or in the future.

Input interface 310 provides an interface for receiving information from the user for entry into computing device 304 as known to those skilled in the art. Input interface 310 may use various input technologies including, but not limited to, a keyboard, a pen and touch screen, a mouse, a track ball, a touch screen, a keypad, one or more buttons, etc. to allow the user to enter information into computing device 304 or to make selections presented in a user interface displayed on display 308. Input interface 310 may provide both an input and an output interface. For example, a touch screen both allows user input and presents output to the user.

Computer-readable medium 312 is an electronic holding place or storage for information so that the information can be accessed by processor 314 as known to those skilled in the art. Computer-readable medium 312 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disk (CD), digital versatile disk (DVD), . . . ), smart cards, flash memory devices, etc. Computing device 304 may have one or more computer-readable media that use the same or a different memory media technology. Computing device 304 also may have one or more drives that support the loading of a memory media such as a CD or DVD.

Processor 314 executes instructions as known to those skilled in the art. The instructions may be carried out by a special purpose computer, logic circuits, or hardware circuits. Thus, processor 314 may be implemented in hardware, firmware, software, or any combination of these methods. The term "execution" is the process of running an application or the carrying out of the operation called for by an instruction. The instructions may be written using one or more programming language, scripting language, assembly language, etc. Processor 314 executes an instruction, meaning that it performs the operations called for by that instruction. Processor 314 operably couples with display 308, with input interface 310, with computer-readable medium 312, and with the communication interface to receive, to send, and to process information. Processor 314 may retrieve a set of instructions from a permanent memory device and copy the instructions in an executable form to a temporary memory device that is generally some form of RAM. Computing device 304 may include a plurality of processors that use the same or a different processing technology.

Data processing application 316 performs operations associated with processing NMR data to identify a concentration equation of a compound and/or to identify chemical characteristics of a mixture using a concentration equation. Some or all of the operations subsequently described may be embodied in data processing application 316. The operations may be implemented using hardware, firmware, software, or any combination of these methods. With reference to the exemplary embodiment of FIG. 3, data processing application 316 is implemented in software stored in computer-readable medium 312 and accessible by processor 314 for execution of the instructions that embody the operations of data processing application 316. Data processing application 316 may be written using one or more programming languages, assembly languages, scripting languages, etc.

Figure 4:
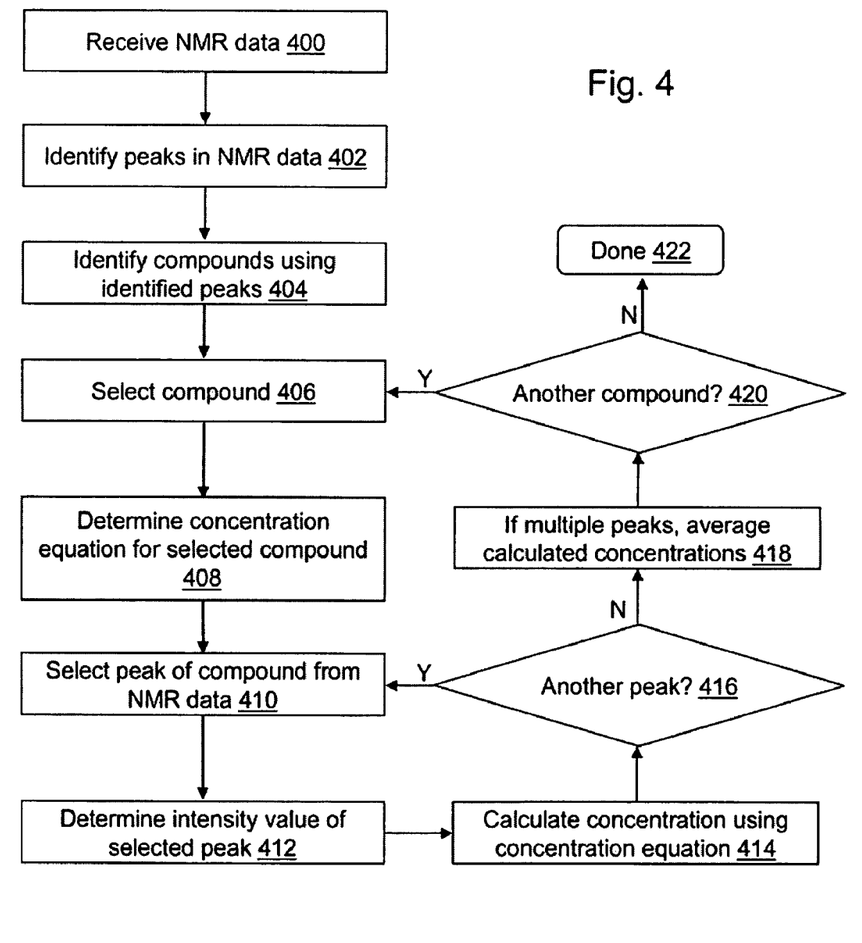
FIG. 4 is a flow diagram illustrating exemplary operations performed by an NMR data processing application in determining a concentration level in accordance with an exemplary embodiment.

With reference to FIG. 4, exemplary operations associated with data processing application 316 identifying chemical characteristics of a mixture using a concentration equation are described. Additional, fewer, or different operations may be performed, depending on the embodiment. The order of the operations is not intended to be limiting. In an operation 400, NMR data are received. For example, the NMR data may be received from NMR spectrometer 302 or may be received from computer-readable medium 312 storing the NMR data. The NMR data also may be received from database 306. The NMR data may include single or multidimensional data generated using NMR spectrometer 302 based on an analysis of mixture 318. In an operation 402, intensity peaks are identified in the received NMR data. For example, the intensity peaks may be identified using NMRPipe, a multidimensional spectral processing system developed by Frank Delaglio et al.

In an operation 404, compounds included in mixture 318 are identified on the basis of observed intensity peaks. For example, the compounds may be identified from information stored in database 306 by cross-referencing the observed $^1H$-$^{13}C$ (or other types) chemical shifts with shifts stored in database 306. The database may be a publicly available one or a proprietary one created by the user for compounds of interest. Additional and/or different methods may be used to identify the compounds included in mixture 318 using the received NMR data. Compound identification may be checked visually by overlaying spectra of pure standards from database 306 onto the NMR spectrum created of mixture 318. In an exemplary embodiment, Sparky, a graphical NMR assignment and integration program developed and maintained at the University of California, San Francisco may be used to prepare the overlaid spectra. In an operation 406, a compound is selected from the identified compounds. For example, a list of compounds included in mixture 318 may be created and a compound selected from the list.

In an operation 408, a concentration equation is determined for the selected compound. The parameters that define the equation can be stored in database 306 and identified using an identifier associated with the selected compound. In an exemplary embodiment, the parameters that define the equation can be derived from spectral information of the selected compound as described with reference to FIG. 8.

Figure 5:
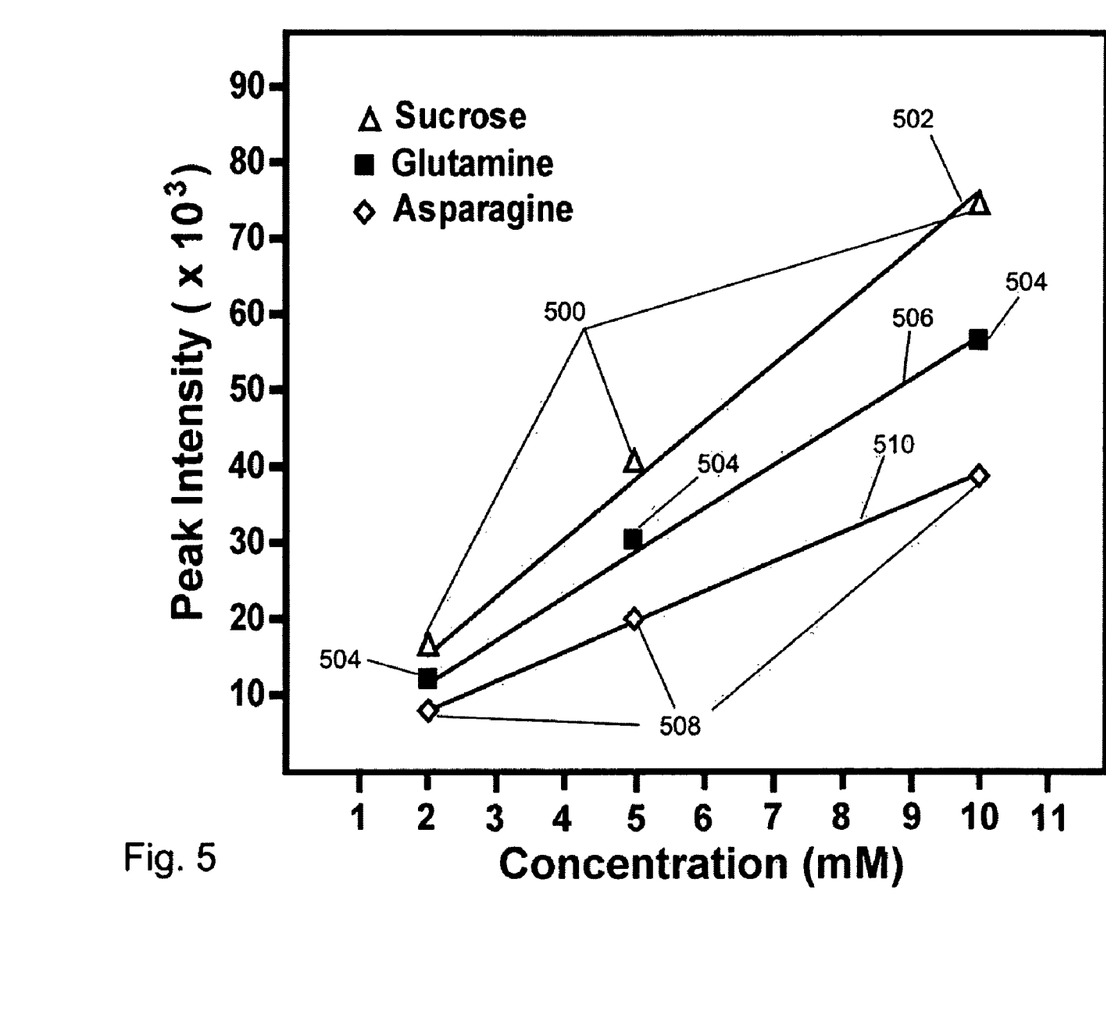
FIG. 5 is a graph of a plurality of concentration curves defined in accordance with an exemplary embodiment.

With reference to FIG. 5, a graph of a plurality of concentration curves is shown in accordance with an exemplary embodiment. A first plurality of data points 500 are used to define a first curve 502 associated with the compound, sucrose. In an exemplary embodiment, the first plurality of data points 500 are peak intensities determined by NMR spectrometer 302 using concentration reference samples of sucrose in mixture 318. For example, concentration reference samples of 2 millimolar (mM), 5 mM, and 10 mM sucrose were used to define the peak intensities of sucrose in mixture 318 though other concentration levels may be used as reference samples. In an exemplary embodiment, the peak intensities of the reference samples may be determined using the same NMR instrument settings for NMR spectrometer 302 used to generate the NMR data received in operation 400. In an exemplary embodiment, the peak intensities of the reference samples may be determined as part of the same experimental process used to generate the NMR data received in operation 400.

A second plurality of data points 504 are used to define a second curve 506 associated with glutamine. Concentration reference samples of 2 mM, 5 mM, and 10 mM of glutamine were used to define the peak intensities of glutamine in mixture 318 though other concentration levels may be used as reference samples. A third plurality of data points 508 are used to define a third curve 510 associated with asparagine. Concentration reference samples of 2 mM, 5 mM, and 10 mM of asparagine were used to define the peak intensities of asparagine in mixture 318 though other concentration levels may be used as reference samples. The reference concentration levels for each compound may be the same or different. Two or more reference concentration levels may be used.

In the exemplary embodiment of FIG. 5, curves 502, 506, 510 are regression lines. As a result, curves 502, 506, 510 may be stored in database 306 using a slope value and an intercept value. In an exemplary embodiment, the intercept value may be assumed to be zero. Other regression curves may be used in alternative embodiments. For example, a higher order polynomial, a conic section, a trigonometric function, etc. may be used to fit the plurality of data points. The concentration equations may be saved using the information associated with the type of curve fit function.

In an exemplary embodiment, high resolution 2D $^1$H-$^{13}$C HSQC NMR data is collected using NMR spectrometer 302 to generate the plurality of data points 500, 504, 508. In another exemplary embodiment, the data collection time may be reduced substantially by allowing aliasing (folding) of the NMR spectrum so long as it does not result in overlapping of the data. NMR data of higher or lower dimensionality may be used in alternative embodiments.

With continuing reference to FIG. 4, in an operation 410, a peak associated with the selected compound is selected from the received NMR data. For example, the received NMR data may include a plurality of peaks associated with the selected compound. In an exemplary embodiment, the selected peak does not overlap with a peak associated either with the same or another identified compound. In an operation 412, an intensity value for the selected peak is determined by a standard method from the received NMR data. For example, the NMR data is analyzed to determine an intensity value(s) associated with or near the selected peak value to determine the intensity value. In an exemplary embodiment, the intensity values of one or more (preferably at least two) non-overlapped peaks from a compound in the mixture may be used to determine the concentration of that compound relative to the intensities of all non-overlapped peaks from an internal standard. For example, HEPES, an organic chemical buffering agent, or Sorbitol may be used as an internal standard. The standard is chosen to be a compound with two or more peaks that do not overlap with peaks of compounds to be quantified. The concentration equation also may have been normalized on the basis of peak intensities of the internal standard if its concentration is known.

In an operation 414, a concentration value of the selected compound in mixture 318 is calculated using the identified concentration equation and the identified intensity value. For example, if a regression line is used to define the concentration equation, the concentration is calculated using $x=^{y-B}/m$ where x is the concentration value, y is the identified intensity value, B is the intercept value of the concentration equation, and m is the slope value of the concentration equation.

In an operation 416, a determination is made concerning whether or not another peak is processed. For example, a user may make a selection initially to define the number of peaks processed. A simple counter or other methods known to those skilled in the art may be used to determine if all of the peaks have been processed. If another peak is to be processed, processing continues at operation 410 to select another peak and calculate another concentration value. If another peak is not to be processed, processing continues at an operation 418. In an exemplary embodiment, at least two well-dispersed peaks belonging to the spin system of the selected compound are selected for processing for each compound. For example, the peaks may be selected based on their being at least three peak widths distant from another peak of intensity greater than 3% of the peak being considered.

In an operation 418, an average of the concentration values calculated in operation 414 is calculated if multiple peaks were processed. In an operation 420, a determination is made concerning whether or not another compound identified in the mixture is yet to be processed. For example, a user may make a selection initially to define a list of compounds to be processed. A simple counter or other methods known to those skilled in the art may be used to determine if all of the compounds selected for processing have been processed. If another compound is to be processed, processing continues at operation 406 where the next compound is chosen. If another compound is not to be processed, processing is complete at an operation 422.

Figure 8:
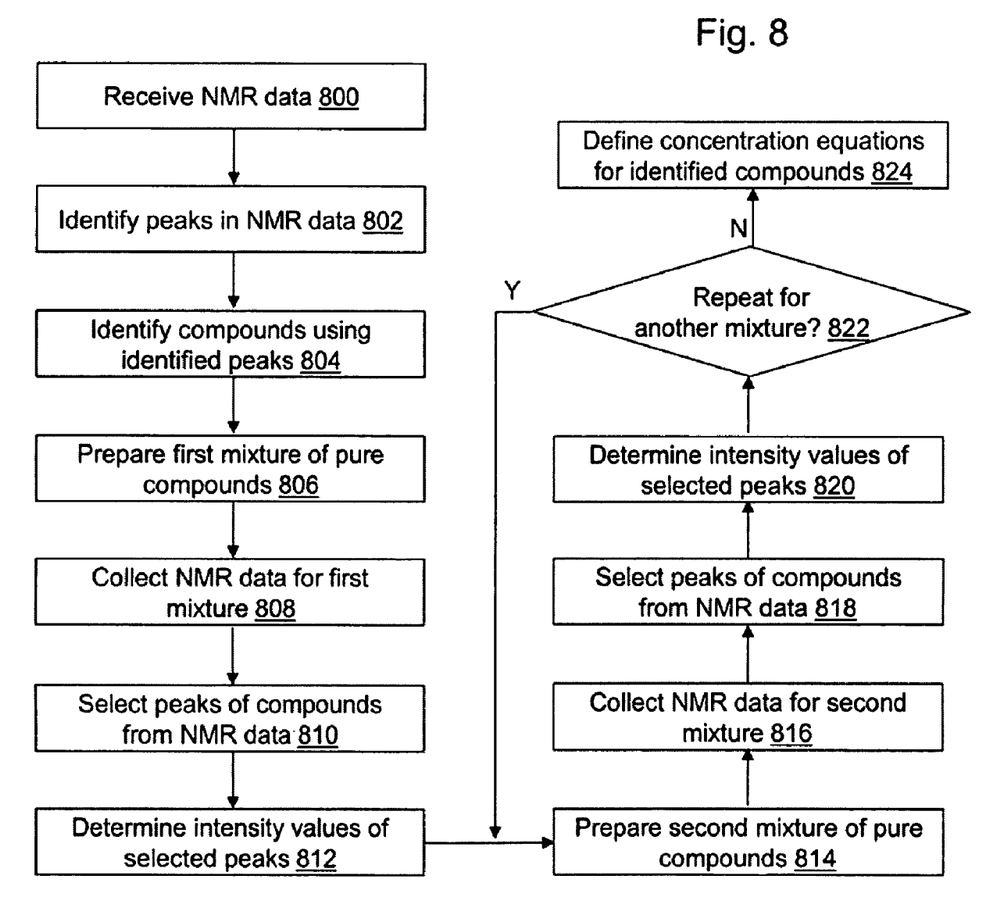
FIG. 8 is a flow diagram illustrating exemplary operations performed by an NMR data processing application in defining a concentration equation in accordance with an exemplary embodiment.

With reference to FIG. 8, additional exemplary operations associated with data processing application 316 of FIG. 3 identifying a concentration equation for a compound are described. Additional, fewer, or different operations may be performed, depending on the embodiment. The order of the operations is not intended to be limiting. The functionality provided by data processing application 316 may be implemented in one or more modules that may be distributed across a plurality of computing devices and that interact to provide the described functionality as known to those skilled in the art. The functionality provided by data processing application 316 may be implemented in one or more modules that may be distributed across a plurality of computing devices and that may execute independently. Thus, data processing application 316 may be implemented as a first data processing application and a second data processing application that execute at the same or different times on the same or different devices and that are integrated with each other or are independent of each other.

In an operation 800, similar to operation 400, NMR data are received. In an operation 802, similar to operation 402, intensity peaks are identified in the received NMR data. In an operation 804, similar to operation 404, compounds included in mixture 318 are identified on the basis of observed intensity peaks. In an operation 806, a first mixture is prepared including pure compounds of the identified compounds at a first concentration known for each compound. In an exemplary embodiment, an equimolar mixture of the pure compounds may be prepared with a first number of moles.

In an operation 808, NMR data are collected for the first mixture. In an operation 810, a peak associated with each of the identified compounds included in the first mixture is selected from the collected NMR data. To reduce the spectrum collection time, the spectrometer settings can be adjusted to allow aliasing (folding) of peaks into the top of the spectral window as long as at least one non-overlapping peak exists for each compound of the identified compounds. The degree of folding that can be tolerated without losing information can be decided on the basis of the peak positions determined for each compound included in the first mixture. In an operation 812, similar to operation 412, an intensity value for each of the selected peaks is determined by a standard method from the collected NMR data. For example, the NMR data is analyzed to determine an intensity value associated with or near the selected peak values to determine the intensity value.

In an operation 814, similar to operation 806, a second mixture is prepared including pure compounds of the identified compounds at a second concentration known for each compound which is different than the first concentration for each pure compound of the identified compounds. In an exemplary embodiment, an equimolar mixture of the pure compounds may be prepared with a second number of moles. In an operation 816, similar to operation 808, NMR data are collected for the second mixture. In an operation 818, similar to operation 810, a peak associated with each of the identified compounds included in the second mixture is selected from the collected NMR data. In an operation 820, similar to operation 812, an intensity value for the selected peaks is determined by a standard method from the collected NMR data.

In operation 822, a determination is made concerning whether or not to repeat the process of operation 814-820 for another mixture. If another mixture is prepared, processing continues in operation 814 with a next mixture prepared including pure compounds of the identified compounds at a next concentration known for each compound which is different than the previous concentrations for each pure compound of the identified compounds. Any number of additional mixtures may be prepared. If another mixture is not prepared, processing continues in an operation 824. In operation 824, concentration equations are defined for each compound of the identified compounds using the intensity values associated with each known concentration for that compound. As known to those skilled in the art, an equation can be defined to fit a plurality of data points. Regression analysis provides an approximate fit to the plurality of data points by minimizing a difference between the plurality of data points and the curve defined by the equation. Thus, in an exemplary embodiment, the concentration equations can be defined using the intensity values determined for each compound at each concentration.

Parallel regressions of 2D $^1$H-$^{13}$C HSQC and 1D $^1$H NMR measurements were obtained using NMR data processing system 300 in accordance with an exemplary embodiment to perform an error analysis comparing 1D $^1$H NMR and 2D $^1$H-$^{13}$C NMR as quantitative tools for metabolic profiling. A subset of NMR-observable metabolites present in *Arabidopsis, Saccharomyces* and *Medicago* extracts was selected to represent an average extract, and several synthetic mixtures of pure compounds were prepared based on the observed metabolites. A total of 30 synthetic mixtures were prepared for the error analysis study. 24 of the samples were designated as "test mixtures", and six samples were designated as "concentration references." Both the test mixtures and the concentration references contained twenty-six small molecules. Twenty-five of these were metabolites selected from a larger list of molecules identified in the three biological extracts. HEPES was also included in the synthetic samples as an internal concentration reference. The test mixtures contained nineteen metabolites with invariant concentrations (all 5 mM) and seven metabolites with variable concentrations ranging from 5.5 to 29.1 mM. The six concentration reference samples were prepared with equimolar mixtures of the twenty-six small molecules. These samples contained each metabolite at 2 mM, 5 mM, or 10 mM.

A separate set of biological concentration reference standards was prepared for estimating concentrations in the three tissue extracts. Biological reference samples had a total of 52 metabolites split between three groups. The groups were designed to minimize overlap between metabolites signals in 2D $^1$H-$^{13}$C NMR spectra. The samples contained 5 mM HEPES as an internal standard. The observed intensities were normalized to the average signal from two dispersed HEPES peaks, and concentration curves were constructed with the HEPES normalized intensities.

Spectra were collected using a Varian 600 MHz spectrometer equipped with a triple-resonance ($^1$H, $^{13}$C, $^{15}$N, $^2$H, lock) cryogenic probe and a sample changer. 1D $^1$H and 2D $^1$H-$^{13}$C HSQC spectra of each sample were collected. The 1D $^1$H spectra were collected using 90° pulses with four acquisitions, four silent scans, an initial delay of 2 seconds (s) and an acquisition time of 2 s. Sensitivity enhanced $^1$H-$^{13}$C HSQC spectra were collected with four scans, 32 silent scans, an initial delay of 1 s and an acquisition time of 0.3 s with broadband decoupling. Quantitative $^1$H-$^{13}$C HSQC spectra were collected in 128 increments using a 70 ppm spectral width in the indirect ($^{13}$C) dimension. The carbon transmitter offset frequency was tuned to allow all aliphatic resonances to be contained within the spectrum. Aromatic resonances and the anomeric resonances of sugars were allowed to wrap into the top of the spectral window. Each quantitative $^1$H-$^{13}$C HSQC spectrum required twelve minutes to collect. With these spectrometer settings, each molecule in the synthetic mixtures yielded at least one non-overlapped cross peak as did each of the identified metabolites in the biological extracts with the exception of putrescine, lactate, and acetate. Thus, to reduce the spectrum collection time, the spectrometer settings can be adjusted to allow aliasing (folding) of peaks into the top of the spectral window as long as at least one non-overlapping peak exists for each compound of interest. The degree of folding that can be tolerated without losing information can be decided on the basis of the peak positions determined for each biological extract.

One high-resolution $^1$H-$^{13}$C HSQC spectrum was collected for each biological extract. These spectra were acquired with 512 increments, 16 scans, and a $^{13}$C spectral width of 140 ppm. High-resolution spectra were used to identify metabolites. The larger spectral width helped avoid resonance assignment errors resulting from spectral folding. The spectra were chemical-shift referenced, phased, Fourier-transformed with a shifted sine bell window function, zero-filled, and peak-picked using automated NMRPipe processing scripts. A list of possible metabolite matches was obtained by cross-referencing observed $^1$H-$^{13}$C chemical shifts (NMR peak locations) with shifts in the Biological Magnetic Resonance Data Bank (BMRB) and Madison Metabolomics Consortium Database databases.

The test samples and concentration reference samples were run as a block under identical acquisition parameters. The sample block was run twice to produce two technical replicates for each sample. To minimize experimental bias, a random number generator was used to determine the sample order. 1D $^1$H and 2D $^1$H-$^{13}$C HSQC spectra were collected sequentially on each sample. Two well-dispersed peaks in the $^1$H-$^{13}$C HSQC spectra were selected for each of the seven target metabolites. A concentration curve was constructed for each metabolite by regressing absolute peak intensities from the concentration reference samples with their known concentrations. The concentration curves were averaged across the technical replicates, and the resulting regression coefficients were used to predict metabolite concentrations in the test samples. Concentration estimates were also averaged across technical replicates to produce a final predicted concentration for each metabolite. Identical procedures were used to estimate concentrations from both 1D and 2D NMR data. Proton chemical shifts used in the 1D $^1$H analysis were those identified from the positions of 2D $^1$H-$^{13}$C HSQC cross peaks.

Figure 6:
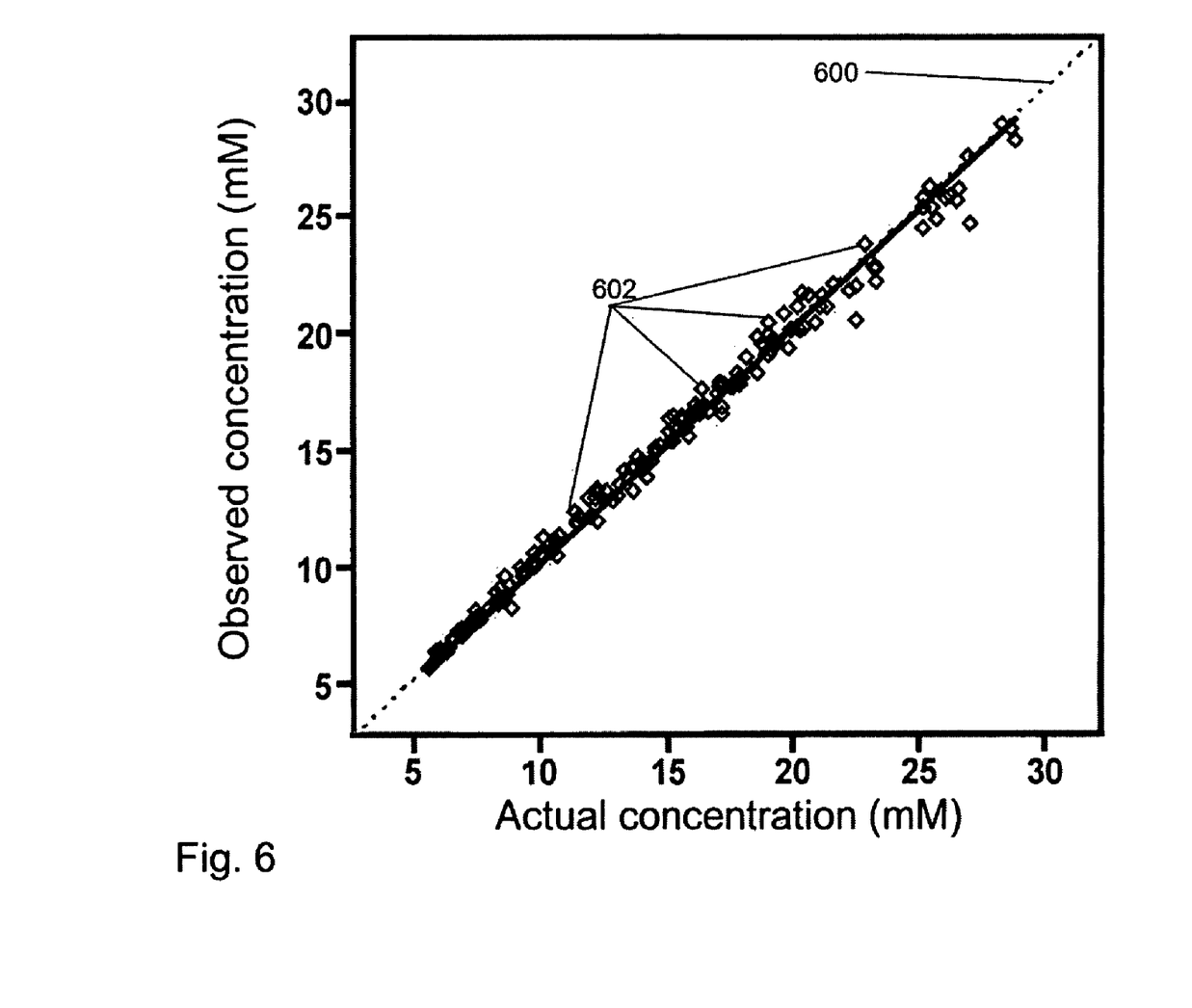
FIG. 6 shows a comparison between an actual concentration of compounds in a mixture and an observed concentration in the mixture determined in accordance with a first exemplary embodiment of the NMR data processing system.

With reference to FIG. 6, a comparison between an actual concentration of compounds in the test samples and an observed concentration in the test samples determined using the 2D $^1$H-$^{13}$C HSQC NMR data is shown. A first regression line 600 indicates an expected comparison line having a slope value of one and an intercept value of zero. A plurality of data points 602 defined using the 2D $^1$H-$^{13}$C HSQC NMR data shows good correspondence with the first regression line 600. A regression line fit to the plurality of data points 602 had a slope value of 0.97 and an intercept value of 0.6 with a percent error of 2.7%. A maximum error of 10.3% also was calculated. This error translated to an average (root mean square) accuracy of 0.6 mM using the 2D $^1$H-$^{13}$C HSQC NMR data. The error estimates were calculated from the divergence of the observed concentration from the actual concentration.

Figure 7:
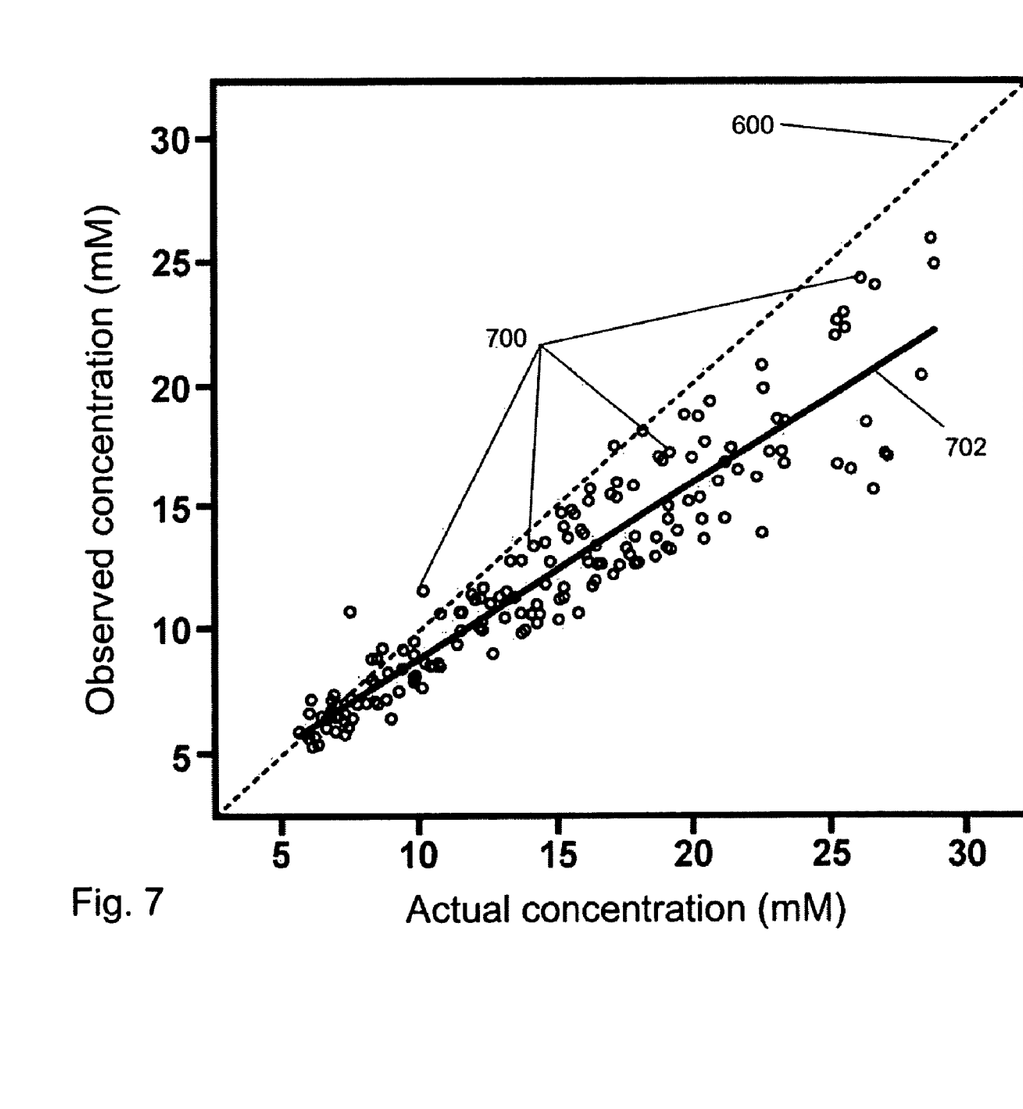
FIG. 7 shows a comparison between an actual concentration of compounds in a mixture and an observed concentration in the mixture determined in accordance with a second exemplary embodiment of the NMR data processing system.

With reference to FIG. 7, a comparison between an actual concentration of compounds in the test samples and an observed concentration in the test samples determined using the 1D $^1$H NMR data is shown. A plurality of data points 700 defined using the 1D $^1$H NMR data were fit to a second regression line 702 having a slope value of 0.71 and an intercept value of 1.9 with a percent error of 16.2%. A maximum error of 44.5% also was calculated. This error translated to an average (root mean square) accuracy of 3.5 mM accuracy using the 1D $^1$H NMR data. Based on a comparison between the parallel regressions of the 2D $^1$H-$^{13}$C HSQC NMR measurements and the 1D $^1$H NMR measurements, the 1D estimates were considerably noisier than the 2D estimates.

The word "exemplary" is used herein to mean serving as an example, instance, or illustration. Any aspect or design described herein as "exemplary" is not necessarily to be construed as preferred or advantageous over other aspects or designs. Further, for the purposes of this disclosure and unless otherwise specified, "a" or "an" means "one or more".

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. Additionally, the functionality described may be implemented in a single executable or application or may be distributed among modules that differ in number and distribution of functionality from those described herein without deviating from the spirit of the invention. Additionally, the order of execution of the functions may be changed without deviating from the spirit of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A concentration determining device comprising:
   a processor; and
   a non-transitory computer-readable medium operably coupled to the processor, the computer-readable medium comprising instructions that, when executed by the processor, perform operations comprising
   (a) identifying a plurality of compounds in a mixture based on intensity peaks identified from nuclear magnetic resonance (NMR) data generated from the mixture;
   (b) selecting a compound from the identified plurality of compounds for a concentration determination;
   (c) determining a concentration equation associated with the selected compound, wherein the concentration equation is defined based on a regression curve fit to a plurality of data points, wherein the plurality of data points are intensity peak values calculated using second NMR data generated for a plurality of reference samples of known concentration levels of the selected compound,
   (d) selecting a first peak associated with the selected compound from the NMR data generated from the mixture, wherein the selected first peak does not overlap with a peak associated with another compound of the identified plurality of compounds;
   (e) determining an intensity value associated with the selected first peak; and
   (f) calculating a concentration value of the selected compound in the mixture using the determined concentration equation and the determined intensity value.

2. The device of claim 1, further comprising a nuclear magnetic resonance spectrometer configured to generate the NMR data.

3. A non-transitory computer-readable medium comprising computer-readable instructions therein that, when executed by a processor, cause a computing device to:
   (a) identify a plurality of compounds in a mixture based on intensity peaks identified from nuclear magnetic resonance (NMR) data generated from the mixture;
   (b) select a compound from the identified plurality of compounds for a concentration determination;
   (c) determine a concentration equation associated with the selected compound, wherein the concentration equation is defined based on a regression curve fit to a plurality of data points, wherein the plurality of data points are intensity peak values calculated using second NMR data generated for a plurality of reference samples of known concentration levels of the selected compound,
   (d) select a first peak associated with the selected compound from the NMR data generated from the mixture, wherein the selected first peak does not overlap with a peak associated with another compound of the identified plurality of compounds;
   (e) determine an intensity value associated with the selected first peak; and
   (f) calculate a concentration value of the selected compound in the mixture using the determined concentration equation and the determined intensity value.

4. A method of determining a concentration value of a compound in a mixture, the method comprising:
   (a) identifying a plurality of compounds in a mixture based on intensity peaks identified from nuclear magnetic resonance (NMR) data generated from the mixture;

(b) selecting a compound from the identified plurality of compounds for a concentration determination;

(c) determining a concentration equation associated with the selected compound, wherein the concentration equation is defined based on a regression curve fit to a plurality of data points, wherein the plurality of data points are intensity peak values calculated using second NMR data generated for a plurality of reference samples of known concentration levels of the selected compound, (d) selecting a first peak associated with the selected compound from the NMR data generated from the mixture, wherein the selected first peak does not overlap with a peak associated with another compound of the identified plurality of compounds;

(e) determining an intensity value associated with the selected first peak; and (f) calculating a concentration value of the selected compound in the mixture using the determined concentration equation and the determined intensity value.

5. The method of claim 4, further comprising:
selecting a second peak associated with the selected compound from the NMR data generated from the mixture; and
repeating (e) and (f) with the selected second peak as the selected first peak.

6. The method of claim 5, further comprising calculating an average of the calculated concentration values as the calculated concentration value.

7. The method of claim 4, further comprising selecting a second compound from the identified plurality of compounds and repeating (c)-(f) with the selected second compound as the selected compound.

8. The method of claim 4, further comprising identifying a plurality of intensity peaks associated with the selected compound from the NMR data generated from the mixture, wherein the first peak is selected from the identified plurality of intensity peaks.

9. The method of claim 4, wherein calculating the concentration value comprises solving the concentration equation for the concentration value using the determined intensity value.

10. The method of claim 4, further comprising, before (a), collecting the NMR data using an NMR spectrometer.

11. The method of claim 4, wherein the plurality of compounds are metabolites.

12. The method of claim 4, wherein the NMR data generated from the mixture is two-dimensional heteronuclear single quantum coherence NMR data.

13. The method of claim 4, wherein the second NMR data is generated in order to allow aliasing as long as an intensity peak of each of the identified compounds does not overlap with the intensity peak associated with another compound of the identified plurality of compounds.

14. The method of claim 4, wherein the concentration equation is normalized based on peak intensities of a standard compound included in the mixture at a known concentration level.

15. The method of claim 4, further comprising normalizing the determined intensity value using a standard intensity peak value associated with a standard compound included in the mixture at a known concentration level.

16. A concentration determining device comprising:
a processor; and
a non-transitory computer-readable medium operably coupled to the processor, the computer-readable medium comprising instructions that, when executed by the processor, perform operations comprising
(a) collecting first NMR data of a first mixture of pure compounds selected from a plurality of compounds, wherein a first concentration of each of the pure compounds in the first mixture is known;

(b) for each of the pure compounds, selecting a first non-overlapping peak from the collected first NMR data;

(c) determining a first intensity value associated with each selected first non-overlapping peak of each of the pure compounds;

(d) collecting second NMR data for a second mixture of the pure compounds, wherein a second concentration of each of the pure compounds in the second mixture is known, and further wherein the second concentration is different from the first concentration;

(e) for each of the pure compounds of the second mixture, selecting a second non-overlapping peak from the collected second NMR data;

(f) determining a second intensity value associated with each selected second non-overlapping peak of each of the pure compounds of the second mixture; and (g) defining a concentration equation for each compound of the pure compounds based on a regression curve fit to the determined first intensity value associated with each pure compound of the first mixture at the first concentration and the determined second intensity value associated with each pure compound of the second mixture at the second concentration, wherein the defined concentration equation is used to determine a concentration of a compound of the pure compounds in a third mixture.

17. The device of claim 16, further comprising a nuclear magnetic resonance spectrometer configured to generate the NMR data generated from the mixture.

18. A non-transitory computer-readable medium comprising computer-readable instructions therein that, when executed by a processor, cause a computing device to:
(a) collect first NMR data of a first mixture of pure compounds selected from a plurality of compounds, wherein a first concentration of each of the pure compounds in the first mixture is known;

(b) for each of the pure compounds, select a first non-overlapping peak from the collected first NMR data;

(c) determine a first intensity value associated with each selected first non-overlapping peak of each of the pure compounds;

(d) collect second NMR data for a second mixture of the pure compounds, wherein a second concentration of each of the pure compounds in the second mixture is known, and further wherein the second concentration is different from the first concentration;

(e) for each of the pure compounds of the second mixture, select a second non-overlapping peak from the collected second NMR data;

(f) determine a second intensity value associated with each selected second non-overlapping peak of each of the pure compounds of the second mixture; and (g) define a concentration equation for each compound of the pure compounds based on a regression curve fit to the determined first intensity value associated with each pure compound of the first mixture at the first concentration and the determined second intensity value associated with each pure compound of the second mixture at the second concentration, wherein the defined concentration equation is used to determine a concentration of a compound of the pure compounds in a third mixture.

19. A method of defining a concentration equation for a compound, the method comprising:

(a) collecting first NMR data of a first mixture of pure compounds selected from a plurality of compounds, wherein a first concentration of each of the pure compounds in the first mixture is known;

(b) for each of the pure compounds, selecting a first non-overlapping peak from the collected first NMR data;

(c) determining a first intensity value associated with each selected first non-overlapping peak of each of the pure compounds;

(d) collecting second NMR data for a second mixture of the pure compounds, wherein a second concentration of each of the pure compounds in the second mixture is known, and further wherein the second concentration is different from the first concentration;

(e) for each of the pure compounds of the second mixture, selecting a second non-overlapping peak from the collected second NMR data;

(f) determining a second intensity value associated with each selected second non-overlapping peak of each of the pure compounds of the second mixture; and (g) defining a concentration equation for each compound of the pure compounds based on a regression curve fit to the determined first intensity value associated with each pure compound of the first mixture at the first concentration and the determined second intensity value associated with each pure compound of the second mixture at the second concentration, wherein the defined concentration equation is used to determine a concentration of a compound of the pure compounds in a third mixture.

20. The method of claim 19, further comprising:

repeating (d)-(f) with a fourth mixture of the pure compounds as the second mixture, wherein a third concentration for each of the pure compounds in the fourth mixture is known, and further wherein the third concentration is different from the first concentration and from the second concentration;

wherein the concentration equation is defined using the additional determined second intensity value associated with each pure compound at the third concentration.

21. The method of claim 19, wherein the concentration equation is normalized based on peak intensities of a standard compound included in the first mixture at a known first concentration level and in the second mixture at a known second concentration level.

22. The method of claim 21, wherein the known first concentration level and the known second concentration level are approximately equal.

23. The method of claim 19, wherein the collected first NMR data is generated to allow aliasing as long as an intensity peak of each of the pure compounds does not overlap with the intensity peak associated with another compound of the pure compounds.

24. The method of claim 19, further comprising normalizing the determined first intensity value using a standard intensity peak value associated with a standard compound included in the first mixture at a known concentration level.

25. The method of claim 19, wherein the plurality of compounds are metabolites.

26. The method of claim 19, wherein the collected first NMR data is two-dimensional heteronuclear single quantum coherence NMR data.

* * * * *